(12) United States Patent
Ong

(10) Patent No.: US 10,843,150 B1
(45) Date of Patent: Nov. 24, 2020

(54) SYSTEM, METHOD AND APPARATUS TO FACILITATE MIXING OF COLOURS TO ACHIEVE DESIRED COLOUR CONSISTENCY

(71) Applicant: Yin Nie Ong, Klang (MY)

(72) Inventor: Yin Nie Ong, Klang (MY)

( * ) Notice: Subject to any disclaimer, the term of this patent is extended or adjusted under 35 U.S.C. 154(b) by 0 days.

(21) Appl. No.: 16/659,322

(22) Filed: Oct. 21, 2019

(51) Int. Cl.
| | | |
|---|---|---|
| *B01F 15/00* | (2006.01) | |
| *G02F 1/01* | (2006.01) | |
| *A61Q 3/02* | (2006.01) | |
| *B01F 15/04* | (2006.01) | |
| *B01F 15/02* | (2006.01) | |

(52) U.S. Cl.
CPC .......... *B01F 15/00253* (2013.01); *A61Q 3/02* (2013.01); *B01F 15/00305* (2013.01); *B01F 15/00311* (2013.01); *B01F 15/0441* (2013.01); *G02F 1/01* (2013.01); *A61K 2800/42* (2013.01); *B01F 15/0202* (2013.01); *B01F 15/0216* (2013.01); *B01F 2215/005* (2013.01); *B01F 2215/0031* (2013.01); *B01F 2215/044* (2013.01); *B01F 2215/0495* (2013.01)

(58) Field of Classification Search
CPC ......... G02F 1/01; A61K 2800/42; A61Q 3/02; B01F 15/00311; B01F 15/00253; B01F 15/00305; B01F 15/0441; B01F 15/0202; B01F 2215/044; B01F 15/0216; B01F 2215/0031; B01F 2215/005; B01F 2215/0495
See application file for complete search history.

(56) References Cited

U.S. PATENT DOCUMENTS

| | | | | |
|---|---|---|---|---|
| 6,782,307 B2 * | 8/2004 | Wilmott | ................ | A61Q 19/00 700/233 |
| 7,206,664 B2 * | 4/2007 | Schmid | ............... | B01F 13/1055 700/239 |
| 7,711,610 B2 * | 5/2010 | Iwaki | ................ | G06Q 30/0621 424/401 |
| 7,877,294 B2 * | 1/2011 | Inzinna, Jr. | .......... | A45D 44/005 705/26.1 |
| 7,963,303 B2 * | 6/2011 | Saranow | ............... | A45D 44/005 141/104 |
| 8,936,390 B2 * | 1/2015 | Hughes | ..................... | B08B 3/02 366/162.1 |
| 9,211,514 B2 * | 12/2015 | Hughes | ..................... | B08B 3/02 |
| 9,999,288 B2 * | 6/2018 | Samain | ................ | A45D 44/005 |
| 10,046,183 B2 * | 8/2018 | Landa | .................... | B65D 83/04 |

(Continued)

*Primary Examiner* — Tony G Soohoo
(74) *Attorney, Agent, or Firm* — Christopher Pilling

(57) ABSTRACT

Method, system, and apparatus to facilitate mixing of at least one colour to achieve a desired colour consistency to perform one or more activities. Particularly, the present system includes multiple user devices, a cloud server, and a colour mixing dispensing apparatus. In operation, multiple user devices are accessible to a user via a user interface to input data by the user to select at least one colour coding parameter. The cloud server includes at least one memory adapted to store data for the at least one colour coding parameter in a colour database and at least one processor that is adapted to execute processor-executable code. In practice, the colour mixing dispensing apparatus is configured to provide instant colour mixing to the user by receiving a set of instructions from the cloud server via a communication network.

9 Claims, 12 Drawing Sheets

(56) References Cited

U.S. PATENT DOCUMENTS

| | | | |
|---|---|---|---|
| 10,232,330 B2* | 3/2019 | Macedo | B01F 15/0237 |
| 10,532,335 B1* | 1/2020 | Chan | B01F 13/1069 |
| 2002/0082745 A1* | 6/2002 | Wilmott | A61K 8/737 |
| | | | 700/233 |
| 2003/0149504 A1* | 8/2003 | Iwaki | G06Q 30/06 |
| | | | 700/117 |
| 2005/0021174 A1* | 1/2005 | Wilmott | B01F 13/1055 |
| | | | 700/233 |
| 2005/0165705 A1* | 7/2005 | Lauper | B01F 13/1055 |
| | | | 705/500 |
| 2009/0218007 A1* | 9/2009 | Saranow | A45D 44/005 |
| | | | 141/104 |
| 2009/0248199 A1* | 10/2009 | Milhorn | B01F 13/1055 |
| | | | 700/239 |
| 2018/0296995 A1* | 10/2018 | Kinnen | B01F 13/1063 |
| 2019/0001288 A1* | 1/2019 | Ciepiel | A47J 43/0716 |
| 2019/0001289 A1* | 1/2019 | Leloup | B01F 5/0685 |
| 2019/0308149 A1* | 10/2019 | Macedo | B01F 13/1058 |

* cited by examiner ically for mood lifting. Colour in the form of paints and polish are utilized in a wide range of applications such as, building and construction industry, in paintings and artistic drawings, protection of various surfaces, inks, emulsifiers, binding agents and wide use in the cosmetic industry.

SYSTEM, METHOD AND APPARATUS TO FACILITATE MIXING OF COLOURS TO ACHIEVE DESIRED COLOUR CONSISTENCY

FIELD OF THE INVENTION

Embodiments of the present invention pertains to system, method and apparatus for facilitating mixing of colours. In particular, for system, method and apparatus for facilitating mixing of colours to achieve colour consistency requested by the user.

BACKGROUND OF THE INVENTION

Human eye has always been intrigued to colours. Over the years colour has always appealed to the human eye for many reasons. Some people have an eye for colour and some are interested in understanding the hue of colours for motivating oneself. Nonetheless one can't deny the relationship of various colour application utilized for different applications and specifically for mood lifting. Colour in the form of paints and polish are utilized in a wide range of applications such as, building and construction industry, in paintings and artistic drawings, protection of various surfaces, inks, emulsifiers, binding agents and wide use in the cosmetic industry.

One of the main product line of cosmetic industry relating to colours is the nail paint industry. A nail paint polish is a liquid that is applied to the human fingernails and toenails in order to decorate them with different colours. Nail paints are a major attraction for a customer and so are the colours associated with the application process to boost one's self esteem. A variety of colours are of a great significance in the nail paint industry due to the fact that colours play a vital role in one's life and also enhance the make-up look of the person and at the same point of time confidence level of the person.

However, in the present time, the nail paint industry reveals a spectrum of fixed colours that are being utilized in the nail paint industry to provide a wide range of nail paint colour. Moreover, the narrow range of colours available in the market shelf is due to the fact that consumer demands are changing constantly. There is no magic wand to understand the growing change in selection of colour line. Therefore, especially in the nail paint industry the manufacturing process is unable to fulfil the demand of different colour combinations. For example, the colour pink is available with glitter and there can be infinite combinations of the colour pink. Furthermore, the time period of manufacturing the nail polish limits the colour range and offers a narrow window of nail paint colours to the customers by the time nail polish product reach the market shelf. Therefore, there remains a need and demand to develop do it yourself (DIY) technology to address the issue at hand.

Generally, Quality control (QC) processes are involved in the manufacturing process of manufacturing paints and nail paints. Quality control processes are performed in order to ensure various parameters like, the colour consistency, the texture of the paint, finishing of the paint, uniformity in colour, adhesive properties of the paint and so on. The quality control processes so involved in the manufacturing process of colour paints are very lengthy and at the same time are very expensive. The expensive cost of the QC process is due to the labour involved in performing the QC task, There are a lot of processes in QC which are very complex, So, in order to perform the QC, it is therefore required to have a good and skilled labour who can perform the task very efficiently.

In the related prior art in this domain, many conventional technologies have been utilized in order to widen the spectrum of colours. However, the conventional technologies available are employed in the nail paint industry do not overcome the problems of hygiene and other health related issues. The use of a nail paint on different customers causes hygiene problems which needs to be addressed.

Another problem related to conventional nail paint technology is the dryness of the nail paint colour. After the purchase of the nail paints, the colour of the nail paints gets dry due to weather conditions. The dryness of the nail paint colour is caused by various factors such as temperature, improper handling procedures and also the chemical composition of the colour. Dryness of the nail paint colour leads to the wastage of the nail polish and also the customer satisfaction is badly affected. There remains a need in the art to consider this issue as well.

Similarly, the packaging of the nail paints in bottle leads to wastage of the product because the portion present in one nail paint bottle is more than required for single application. This is generally due to the fact that people apply that nail paint only once, So the nail paint in that bottle is more than enough for one application and hence leads to wastage of the nail paint. Moreover, the conventional technologies are not user-friendly which leads to the scope of a new invention in this particular field to fill the gaps and develop efficient system to tackle the above mentioned issues.

In view of the foregoing, there remains a need in the art to develop for a nail paint colour selection system which can reduce the storage space of hundreds of nail paint bottles, enhance the hygiene of the customer, reduce the wastage of nail paints and also give rise to infinite nail paint colour range for the customer.

Thus, there remains a need in the art for system, method and apparatus for facilitating mixing of colours. Accordingly, the present invention relates to the system, method and apparatus for facilitating mixing of colours based on colour code recipe data provided by user.

SUMMARY OF THE INVENTION

Embodiments of the present disclosure relate to methods, and systems, and apparatus to facilitate mixing of at least one colour to achieve a desired colour consistency to perform one or more activities. Particularly, the present system includes multiple user devices, a cloud server, and a colour mixing dispensing apparatus. In operation, multiple user devices are accessible to a user via a user interface to input data by the user to select at least one colour coding parameter. The cloud server includes at least one memory adapted to store data for the at least one colour coding parameter in a colour database and at least one processor that is adapted to execute processor-executable code. In practice, the colour mixing dispensing apparatus is configured to provide instant colour mixing to the user by receiving a set of instructions from the cloud server via a communication network.

In accordance with various embodiments of the present invention, the colour mixing dispensing apparatus includes a dispensing housing unit. The dispensing housing unit is configured to house multiple dispensers and each dispenser is housing a colour composition in a cartridge member. Further, the apparatus includes a controller module and the controller module includes a dosing sub-module configured to control dispense the desired colour consistency based on data received from the user via the communication network. In use, a cartridge is configured to dispense the desired colour consistency composition to perform the one or more activities, and a collector member to receive the desired colour consistency composition from one or more dispensers from each of the cartridge.

In one embodiment of the present invention, the processor in response to execution, enables the cloud server to perform actions, including, for each module of multiple modules on the colour mixing dispensing apparatus and each module of the multiple modules are capable of being used interoperably with other modules and multiple sub-modules without altering the other modules and sub-modules.

In another embodiment of the present invention, the present method facilitate mixing of one or more colours to achieve the desired colour consistency to perform one or more activities. Particularly, the method includes the steps of receiving input data, storing the input data, processing the input data, communicating the input data to the colour mixing dispensing apparatus via the communication network, determining dispensing of the desired colour consistency based on the input data and generating instant colour mixing colour composition by the colour mixing dispensing apparatus.

BRIEF DESCRIPTION OF THE DRAWINGS

So that the manner in which the above recited features of the present invention is to be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 7A, FIG. 7B and FIG. 70 illustrates a pictorial representation of different components of the colour mixing dispensing apparatus, according to one or more embodiments of the present invention;

ELEMENT LIST

Figure 1:
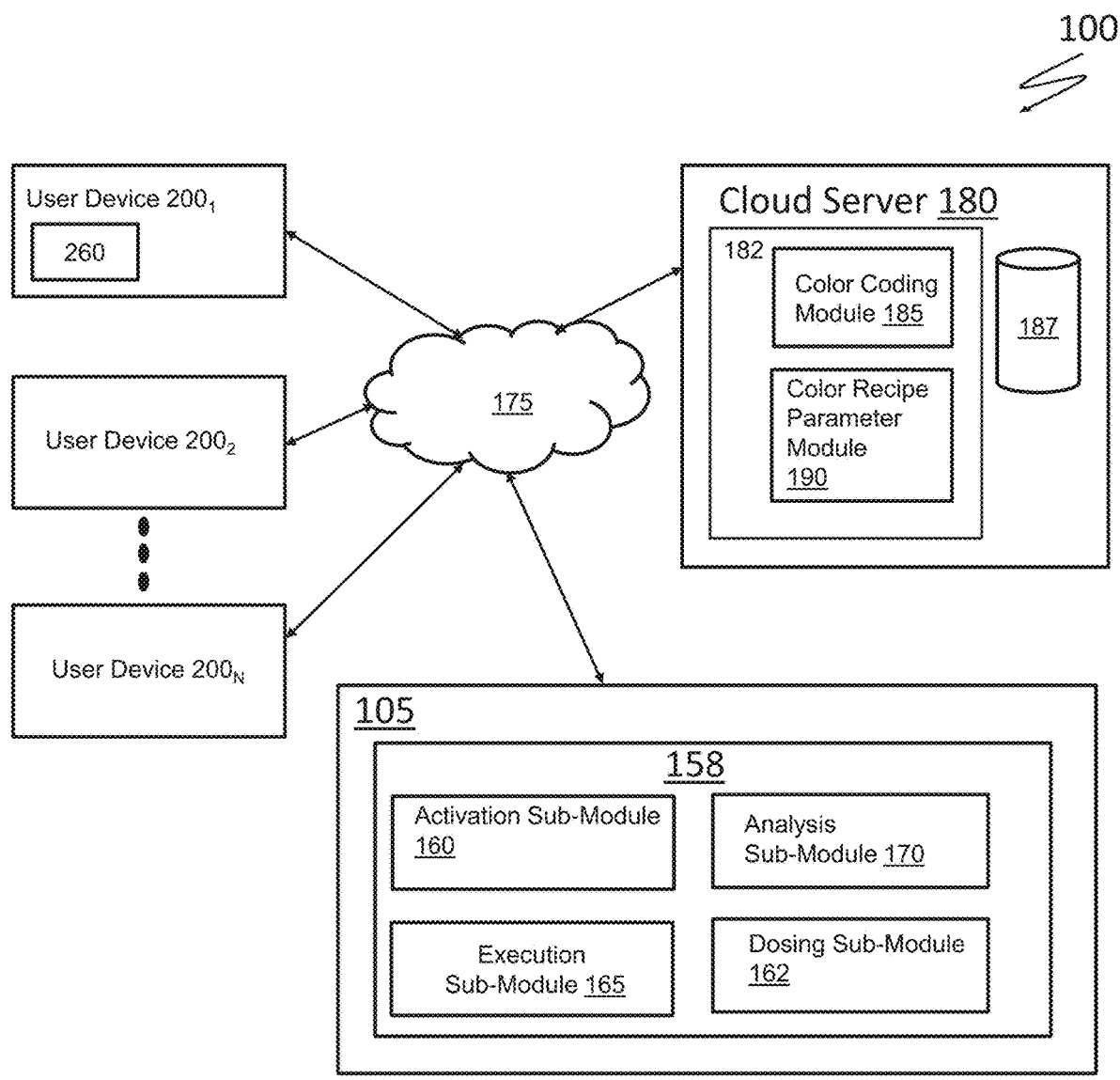
FIG. 1 illustrates a block diagram of schematic configuration of a system to facilitate mixing of at least one colour to achieve a desired colour consistency to perform one or more activities, according to one embodiment of the present invention.

Colour Mixing Dispensing Apparatus 105
Dispensing housing unit 110
Housing 120
Input Interface 260
Drive Gear 125
Controller Member 108
Sensor 130
Cartridge 135
Cartridge Holder 140
Dispenser User Interface 145
Dispenser 150
Power Controller 155
User Device 200
Cloud Server 180
Colour Coding Module 185
Collector Member 192
Colour Recipe Parameter Module 190
Colour database 187
Activation Sub-Module 160
Execution Sub-module 165
Communication network 175
Elongated Member 127
Analysis Sub-module 170
Controller Module 158
Dosing Sub-module 162
Processor 182

DETAILED DESCRIPTION

The present invention relates to system, colour mixing dispensing apparatus and method for producing consistent colour to perform one or more activities. Particularly, the one or more activities is any one selected from nail paint, gel for nail polish, hair colour, hair dye, face foundation and beauty cosmetic product. Moreover, the present invention relates to system, colour mixing dispensing apparatus and method to facilitate mixing of one or more colours to achieve a desired colour consistency to perform one or more activities. The principle of the present invention and their advantages are best understood by referring to FIG. 1 to FIG. 9. In the following detailed description of illustrative or exemplary embodiments of the disclosure, specific embodiments in which the disclosure may be practiced are described in sufficient detail to enable those skilled in the art to practice the disclosed embodiments.

The following detailed description is, therefore, not to be taken in a limiting sense, and the scope of the present disclosure is defined by the appended claims and equivalents thereof. References within the specification to "one embodiment," "an embodiment," "embodiments," or "one or more embodiments" are intended to indicate that a particular feature, structure, or characteristic described in connection with the embodiment is included in at least one embodiment of the present disclosure.

Various embodiments of the present invention provide a method for facilitating mixing of one or more colours to achieve a desired colour consistency to perform one or more activities. Particularly, the method includes the steps of receiving input data, storing the input data, processing the input data, communicating the input data to the colour mixing dispensing apparatus via the communication network, determining dispensing of the desired colour consistency based on the input data and generating instant colour mixing colour composition by the colour mixing dispensing apparatus.

FIG. 1 illustrates a block diagram of schematic configuration of a system 100 to facilitate mixing of at least one colour to achieve the desired colour consistency to perform one or more activities, according to one embodiment of the present invention. With reference now to the Figs, particularly like reference numbers denote parts and different components of the present system 100, The present system 100 includes multiple user devices 200, a cloud server 180, and a colour mixing dispensing apparatus 105 configured to communicate via execution of a set of instructions from through a communication network 175.

In operation, the multiple user devices $200_1$, $200_2$, ..., $200_N$ are accessible to one or more users via a user interface 260 to input data. By utilizing the user interface 260 the user is able to input data to select one or more colour coding parameters to obtain the desired colour consistency composition of the colour to perform one or more activities. The input data is communicated to the cloud server 180 for further analysis via the communication network 175.

In accordance with another embodiment of the present invention, the one or more colour coding parameters are selected from the multiple different viscosity range to achieve the desired colour consistency composition in response to the input data received by the user.

In accordance with one embodiment of the present invention, the cloud server 180 includes at least one memory adapted to store data received from the user via the communication network 175. Particularly, the data obtained is the data for the one or more colour coding parameters. In operation, the data obtained is stored in a colour database 187, The processor 182 of the cloud server 180 is adapted to execute processor-executable code and the data obtained is executed by the processor 182.

In another embodiment of the present invention, the colour database 187 also stores data related to real time updates, usage support and analysis.

In accordance with yet another embodiment of the present invention, the processor 182 in response to execution, enables the cloud server 180 to perform actions, including, for each module of multiple modules on the colour mixing dispensing apparatus 105 via the communication network 175. In operation, each module of the multiple modules is capable of being used interoperably with other modules and multiple sub-modules without altering the other modules and sub-modules of the present system 100.

In accordance with yet another embodiment of the present invention, the cloud server 180 includes a colour coding module 185 and a colour recipe parameter module 190. Practically, the colour coding module 185 is configured to process the data received from the user and store the data in the colour database 187. Further, the colour recipe parameter module 190 is configured to execute and analyse the data received from colour coding module 185. Once the data received from colour coding module 185 are analysed the set of instructions for instant colour mixing is provided to the colour mixing dispensing apparatus 105 via the communication network 175 to be operated a defined time frame.

In accordance with yet another embodiment of the present invention, the defined time frame is any one selected from a pre-defined time period and real time operation of the colour mixing dispensing apparatus 105.

Practically, the colour mixing dispensing apparatus 105 of the present system 100 is configured to provide instant colour mixing to the user by receiving the set of instructions from the cloud server 180 via the communication network 175. In use, the colour mixing dispensing apparatus 105 includes a dispensing housing unit 110 (FIG. 3) and a controller module 158 to execute and compute one or more set of instructions received by the cloud server 180. The dispensing housing unit 110 includes multiple dispensers 150 and each 150 is housing a colour composition in a cartridge member 135 as illustrated in FIG. 5 of the present invention.

Figure 4:
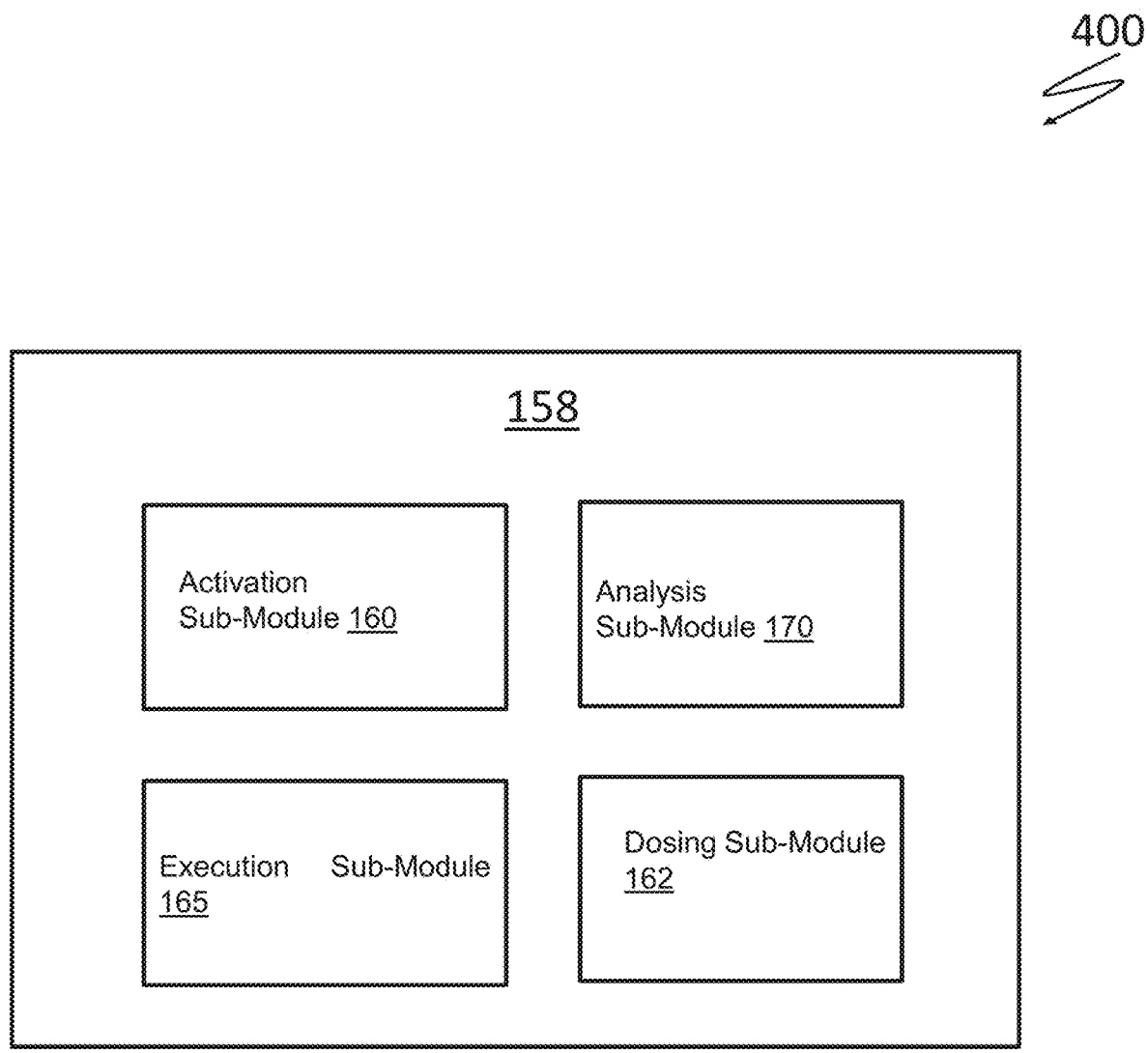
FIG. 4 illustrates a block diagram illustrating a controller module of the colour mixing dispensing apparatus, according to one or more embodiments of the present invention.

FIG. 4 illustrates a block diagram 400 illustrating the controller module 158 of the colour mixing dispensing apparatus 105, according to one or more embodiments of the present invention. Particularly, the controller module 158 includes a dosing sub-module 162, an activation sub-module 160, an execution sub-module 160 and an analysis sub-module 170. In operation, the dosing sub-module 162 is configured to control quantity of colour to be dispensed via one or more dispensers 150 to obtain the desired colour consistency composition based on data received from the user via the communication network 175.

Figure 3:
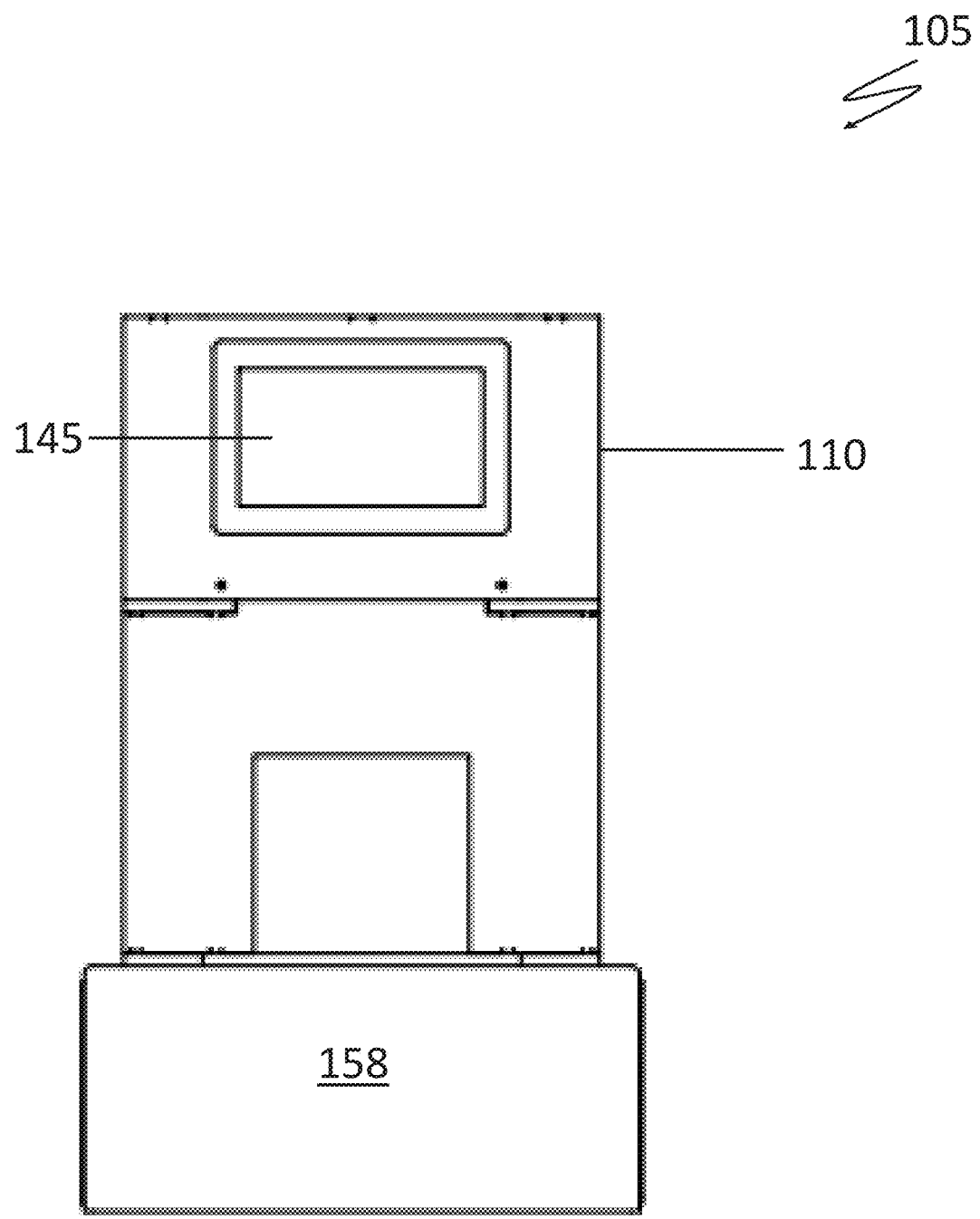
FIG. 3 illustrates a pictorial representation of a front view of a colour mixing dispensing apparatus, according to one or more embodiments of the present invention.
Figure 5:
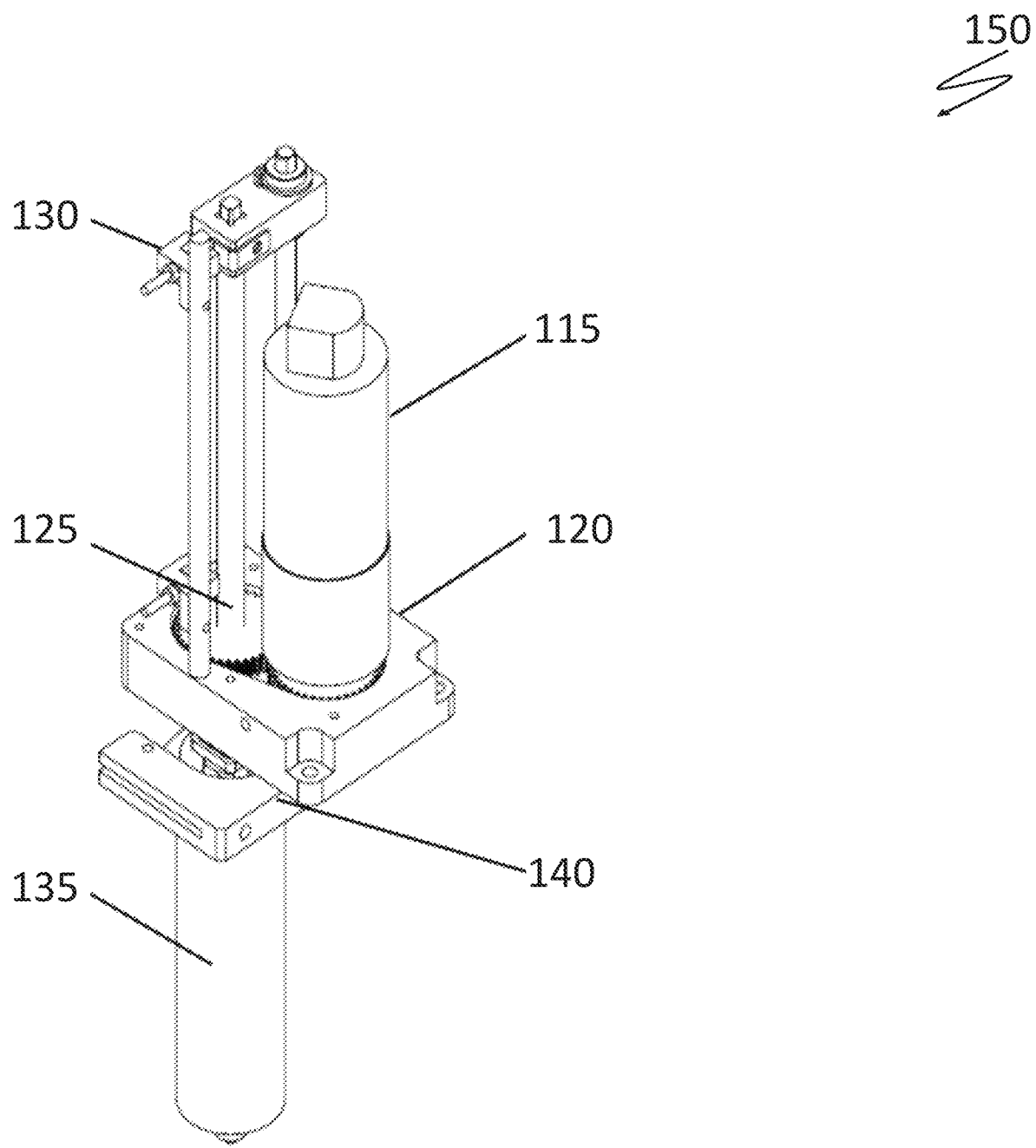
FIG. 5 illustrates an isometric view of the dispenser of the colour mixing dispensing apparatus, according to one or more embodiments of the present invention.
Figure 6:
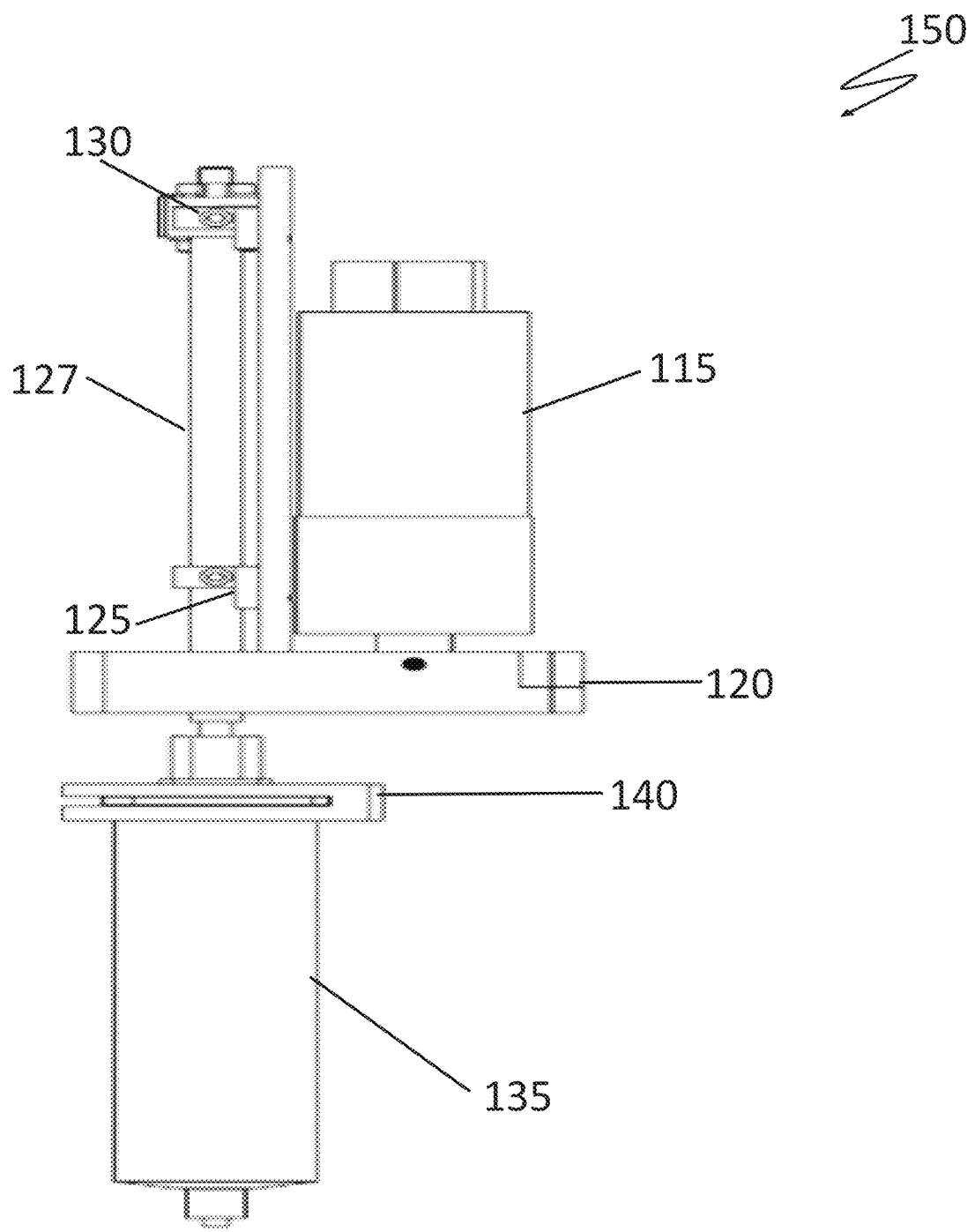
FIG. 6 illustrates a side view of the dispenser of the colour mixing dispensing apparatus, according to one or more embodiments of the present invention.

FIG. 5 illustrates an isometric view of the dispenser 150 of the colour mixing dispensing apparatus 105, and FIG. 6 illustrates a side view of the dispenser 150 of the colour mixing dispensing apparatus 105, according to one or more embodiments of the present invention. The controller module 158 is in electronic communication with a dispenser user interface 145 and electrically powered by a power controller 155 as illustrated in FIG. 3 of the present invention. Particularly, the activation sub-module 160 is configured to receive the set of instructions via the communication network 175 to activate operation of the controller member 108 to drive one or more drive gears 125 by validating and making a determination of colour code recipe data provided by the user. Subsequently, the analysis sub-module 170 is configured to analyse the one or more parameters and the execution sub-module 165 is configured to execute the one or more parameters sensed by the one or more sensors 130.

In accordance with one embodiment of the present invention, the one or more parameters sensed by the one or more sensors 130 are selected from anyone of a minimum volume dispersion of one or more desired colour consistency composition dispensed from one or more cartridge members 135 and multiple different viscosity range of the colour composition.

As illustrated in FIG. 5, the cartridge member 135 is configured to dispense the desired colour consistency composition to perform the one or more activities to end user based on the data received via the cloud server 180. Particularly, each dispenser 150 deployed in the colour mixing dispensing apparatus 105 includes a controller member 108, a drive gear 125, an elongated member 127 configured to mate with the one drive gear 125 and the sensor 130 is positioned over the elongated member 127 to provide sensing of the one or more parameters and a cartridge holder means 140.

In operation, the controller member 108 is configured to provide motorized control for operating the dispensing housing unit 110. The drive gear 125 is further configured to mate with the controller member 108. Particularly, the cartridge holder means 140 holds the cartridge member 135 in position to dispense the desired colour consistency composition.

In accordance with another embodiment of the present invention, the controller member 108 configured to provide air pressure control mechanism for operating the dispensing housing unit 110.

In accordance with one embodiment of the present invention, the cartridge member 135 is configured with a drip protection mechanism of discharging the desired colour consistency composition based on the set of instructions retrieved from the colour recipe parameter module 190.

In one embodiment, the controller member 108 is a DC motor.

Figure 7A:
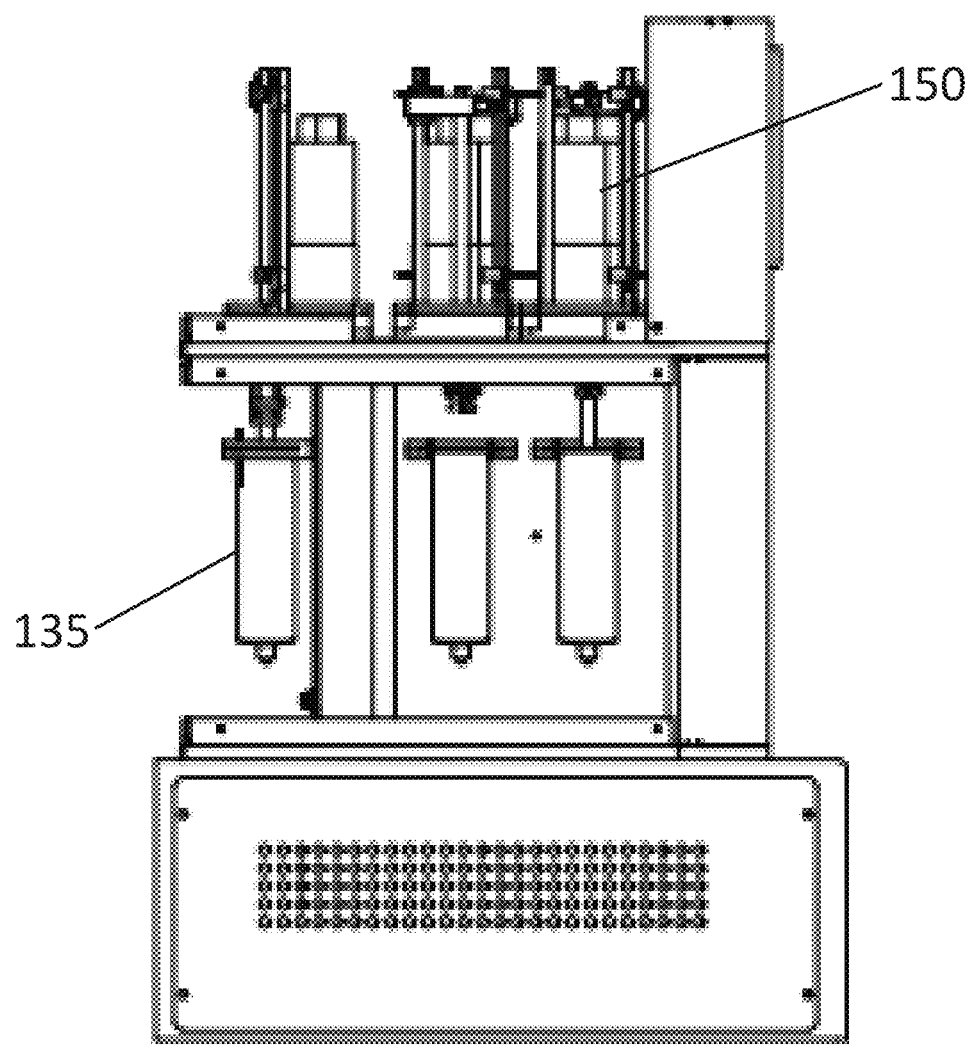
Figure 7B:
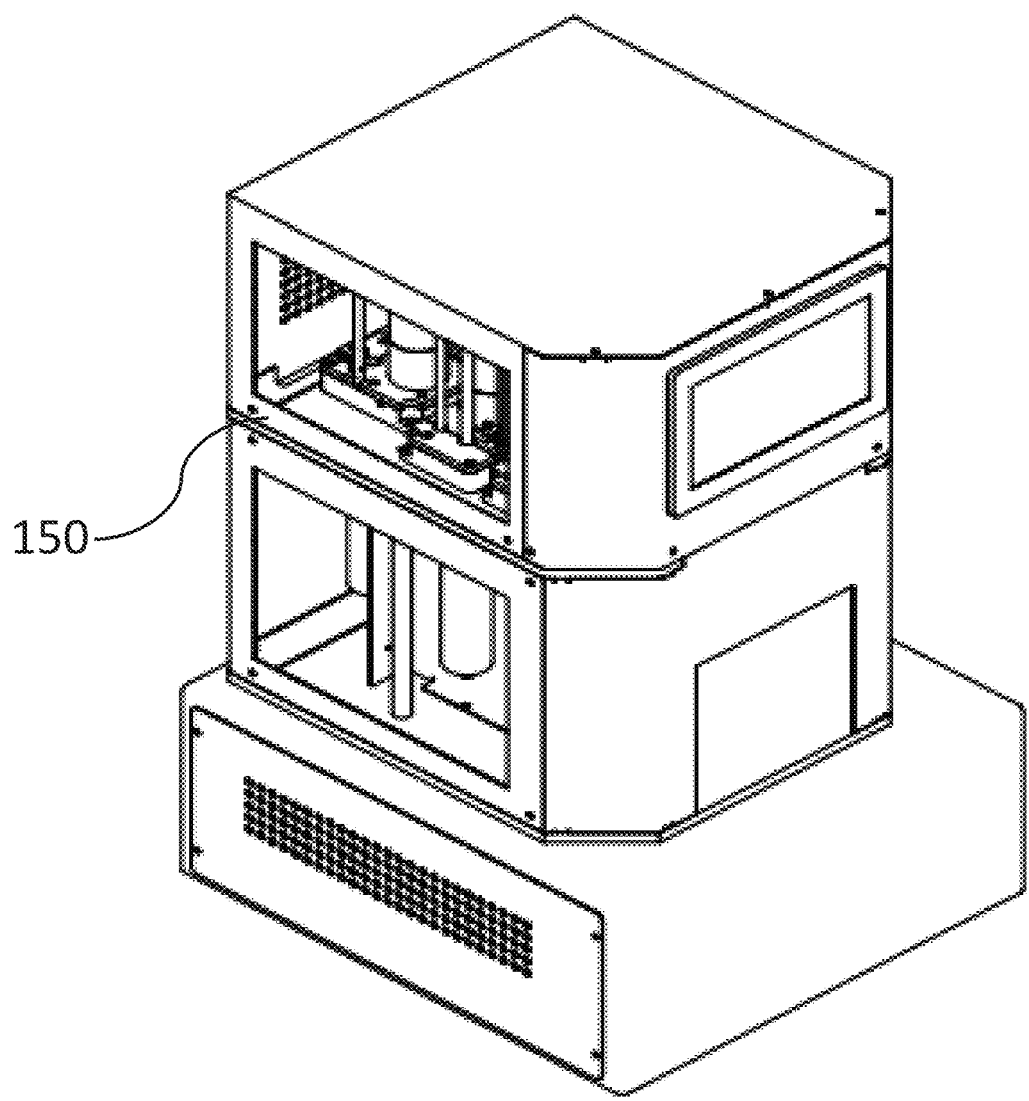
Figure 7C:
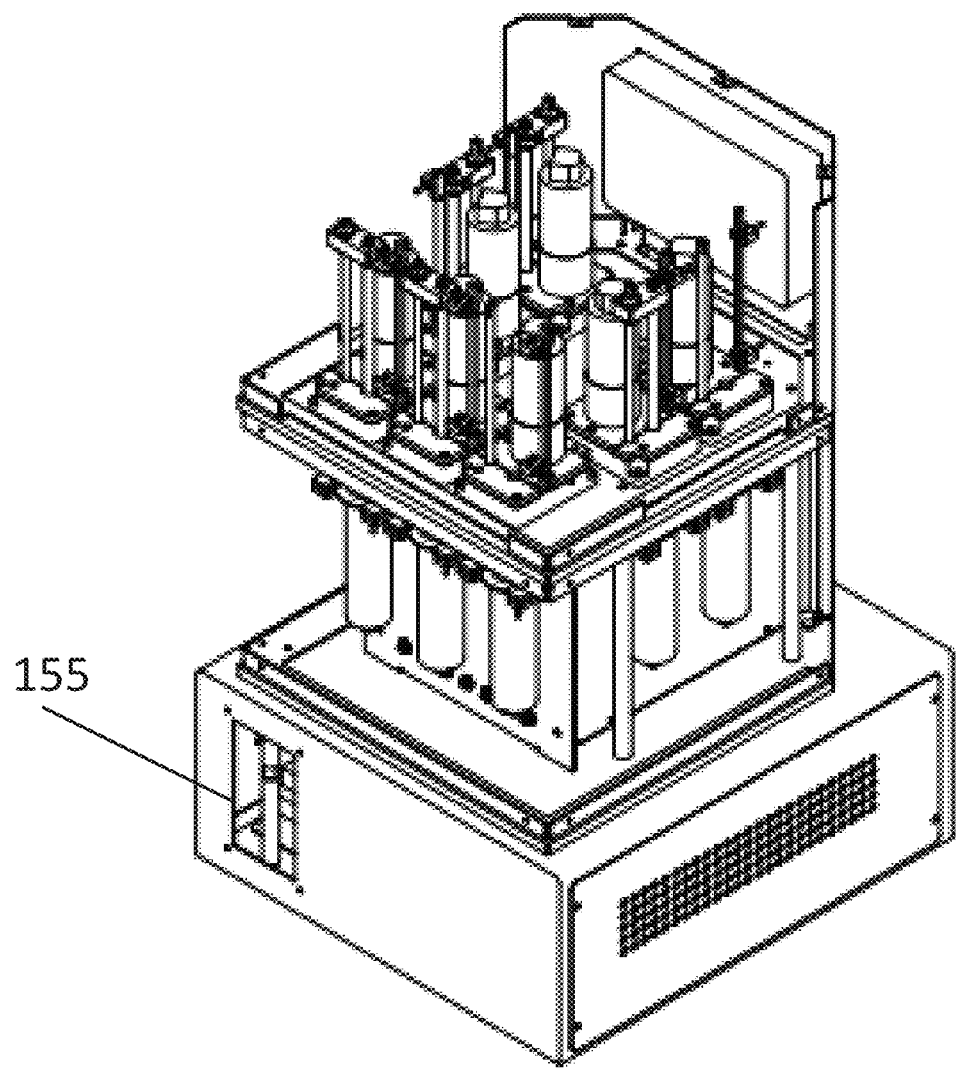
Figure 7D:
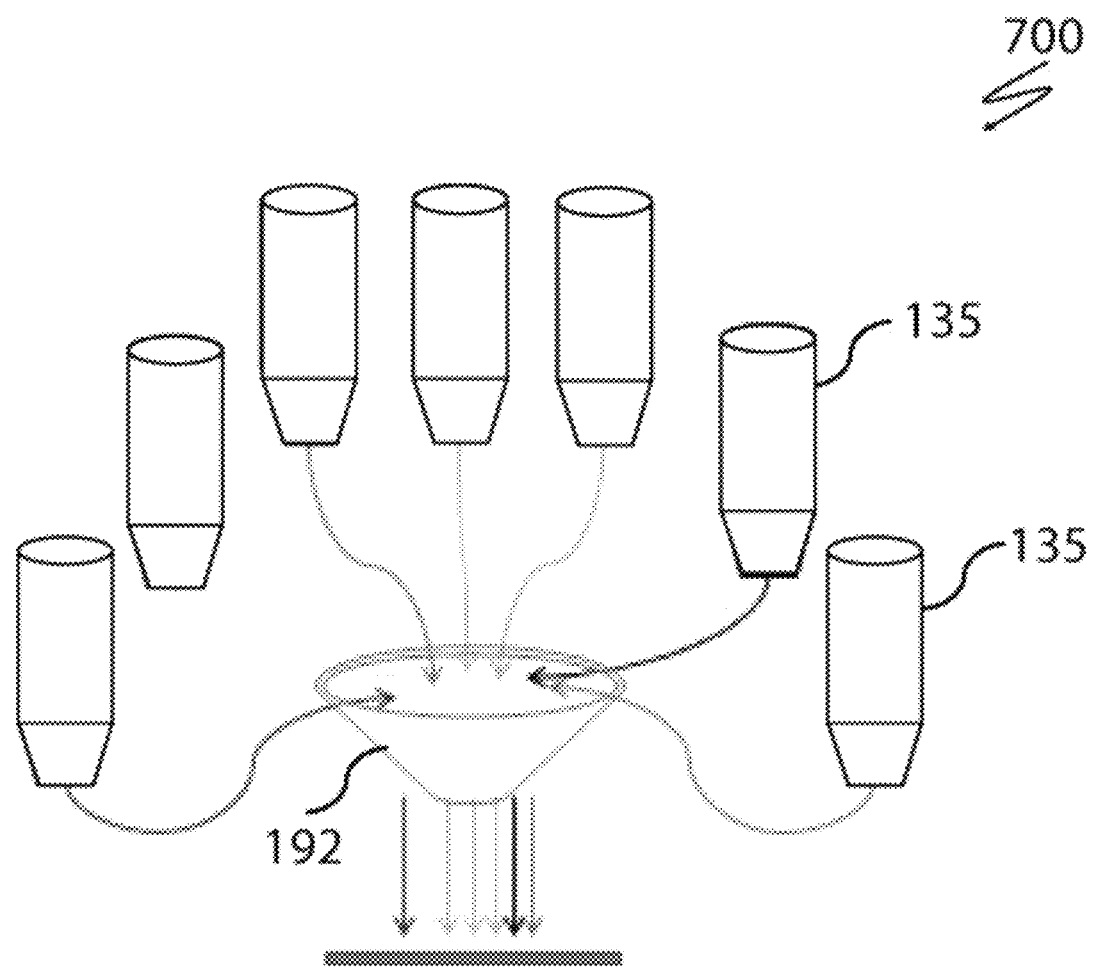
FIG. 7D illustrates a pictorial representation of each cartridge member dispensing measured quantity of colour into a collector member based on input data received via a communication network to the colour mixing dispensing apparatus, according to one or more embodiments of the present invention.

FIG. 7D illustrates a pictorial representation 700 of each cartridge member 135 dispensing measured quantity of colour into the collector member 192 based on input data received via the communication network 175 to the colour mixing dispensing apparatus 105, according to one or more embodiments of the present invention. In practice, the user operating the colour mixing dispensing apparatus 105 loads every cartridge member 135 with different colour for smooth operation of the present system 100. The user inputs the data through the user device 200 and the data is communicated to the cloud server 180. The data is further received by the colour mixing dispensing apparatus 105 and the set of instructions are executed by the controller module 158 to communicate the data to each dispenser 150 to dispense measured quantity of colour into the collector member 192 via the individual cartridge member 135 of dispenser 150. In use, the collector member 192 is able to receive at desired colour consistency composition from at least one dispenser 150 from the cartridge member 135.

Figure 2:
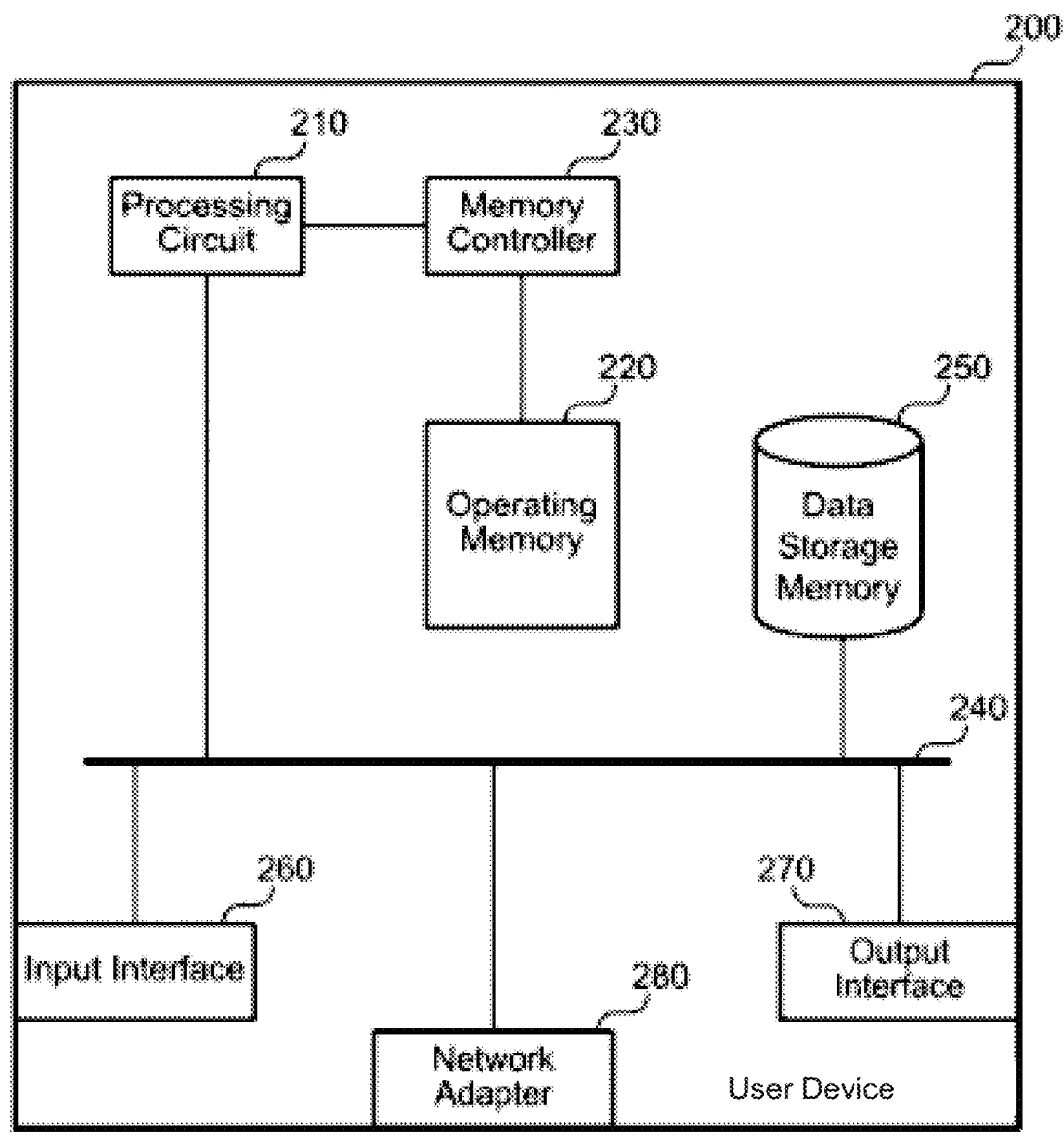
FIG. 2 is a block diagram illustrating one example of a suitable user device, according to one or more embodiments of the present invention.

FIG. 2 is a block diagram illustrating one example of a suitable user device 200, according to one or more embodiments of the present invention. The user device 200 may be virtually any type of general- or specific-purpose computing device. For example, user device 200 may be a user device such as a desktop computer, a laptop computer, a tablet computer, a display device, a camera, a printer, or a smartphone. Likewise, user device 200 may also be server device such as an application server computer, a virtual computing host computer, or a file server computer, e.g., user device 200 may be an example of user device 200 or cloud server 180 of FIG. 1.

User device 200 may also be an IoT device that connects to a network to receive IoT services. As illustrated in FIG. 2, user device 200 includes processing circuit 210, operating memory 220, memory controller 230, data storage memory 250, input interface 260, output interface 270, and network adapter 280. Each of these afore-listed components of user device 200 includes at least one hardware element. User device 200 includes at least one processing circuit 210 configured to execute instructions, such as instructions for implementing the herein-described execution of set of instructions, processes, or technology. Processing circuit 210 may include a microprocessor, a microcontroller, a graphics processor, a coprocessor, a field-programmable gate array, a programmable logic device, a signal processor, or any other circuit suitable for processing data. Processing circuit 210 is an example of a core. The aforementioned instructions, along with other data (e.g., datasets, metadata, operating system instructions, etc.), may be stored in operating memory 220 during run-time of computing device 200. Operating memory 220 may also include any of a variety of data storage devices/components, such as volatile memories, semi-volatile memories, random access memories, static memories, caches, buffers, or other media used to store run-time information.

In one example, operating memory 220 does not retain information when user device 200 is powered off. Rather, user device 200 may be configured to transfer instructions from a non-volatile data storage component (e.g., data storage component 250) to operating memory 220 as part of a booting or other loading process. In some examples, other forms of execution may be employed, such as execution directly from data storage memory 250, e.g., eXecute In Place (XIP), Operating memory 220 may include 4th generation double data rate (DDR4) memory, 3rd generation double data rate (DDR3) memory, other dynamic random access memory (DRAM), High Bandwidth Memory (HBM), Hybrid Memory Cube memory, 3D-stacked memory, static random access memory (SRAM), magnetoresistive random access memory (MRAM), pseudostatic random access memory (PSRAM), or other memory, and such memory may comprise one or more memory circuits integrated onto a DIMM, SIMM, SODIMM, Known Good Die (KGD), or other packaging. Such operating memory modules or devices may be organized according to channels, ranks, and banks. For example, operating memory devices may be coupled to processing circuit 210 via memory controller 230 in channels. Memory controller 230 is configured to interface processing circuit 210 to operating memory 220. For example, memory controller 230 may be configured to interface commands, addresses, and data between operating memory 220 and processing circuit 210. Memory controller 230 may also be configured to abstract or otherwise manage certain aspects of memory management from or for processing circuit 210. In user device 200, data storage memory 250, input interface 260, output interface 270, and network adapter 280 are interfaced to processing circuit 210 by bus 240.

Although, FIG. 2 illustrates bus 240 as a single passive bus, other configurations, such as a collection of buses, a collection of point to point links, an input/output controller, a bridge, other interface circuitry, or any collection thereof may also be suitably employed for interfacing data storage memory 250, input interface 260, output interface 270, or network adapter 280 to processing circuit 210. In user device 200, data storage memory 250 is employed for long-term non-volatile data storage. Data storage memory 250 may include any of a variety of non-volatile data storage devices/components, such as non-volatile memories, disks, disk drives, hard drives, solid-state drives, or any other media that can be used for the non-volatile storage of information. User device 200 also includes input interface 260, which may be configured to enable user device 200 to receive input from users or from other devices. In addition, User device 200 includes output interface 270, which may be configured to provide output from computing device 200. In one example, output interface 270 includes a frame buffer, graphics processor, graphics processor or accelerator, and is configured to render displays for presentation on a separate visual display device (such as a monitor, projector, virtual computing client computer, etc.). In the illustrated example, user device 200 is configured to communicate with other computing devices or entities via network adapter 280. Network adapter 280 may include a wired network adapter, e.g., an Ethernet adapter, a Token Ring adapter, or a Digital Subscriber Line (DSL) adapter. Network adapter 280 may also include a wireless network adapter, for example, a Wi-Fi adapter, a Bluetooth adapter, a ZigBee adapter, a Long Term Evolution (LTE) adapter, SigFox, LoRa, Powerline, or a 5G adapter. Although user device 200 is illustrated with certain components configured in a particular arrangement, these components and arrangement are merely one example of a computing device in which the technology may be employed. In other examples, data storage memory 250, input interface 260, output interface 270, or network adapter 280 may be directly coupled to processing circuit 210, or be coupled to processing circuit 210 via an input/output controller, a bridge, or other interface circuitry, Other variations of the technology are possible.

Figure 8:
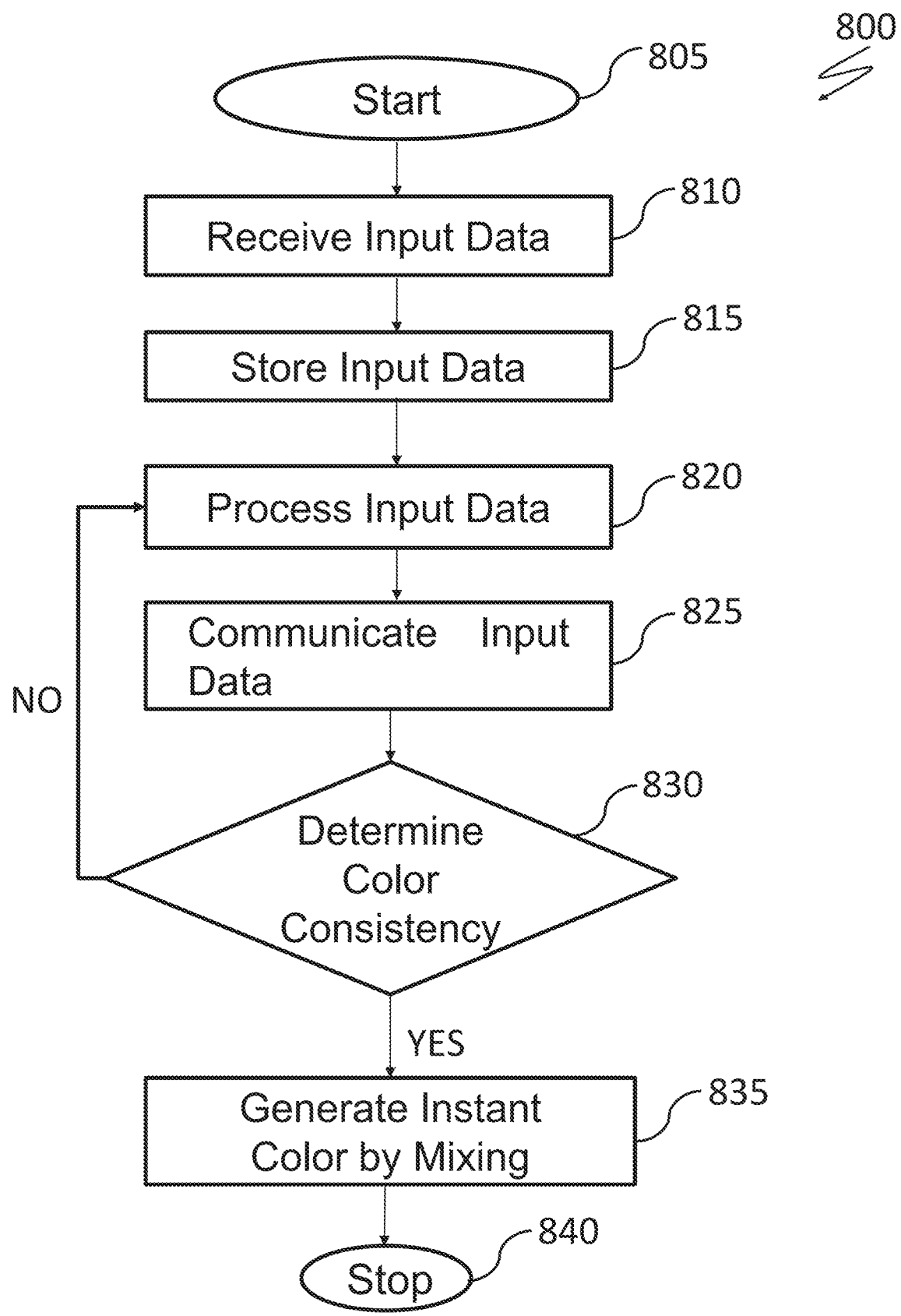
FIG. 8 is a flowchart illustrating a method to facilitate mixing of at least one colour to achieve the desired colour consistency to perform one or more activities, according to one or more embodiments of the present invention.

FIG. 8 is a flowchart illustrating a method 800 to facilitate mixing of at least one colour to achieve a desired colour consistency to perform one or more activities, according to one or more embodiments of the present invention. The achieved desired colour consistency is utilized for the one or more activities selected from and not limited to anyone of nail paint, gel for nail polish, hair colour, hair dye, face foundation and beauty cosmetic product. The method 800 starts at step 805 and proceeds to step 810. At step 810, multiple user devices $200_1$, $200_2$, $200_N$ are accessible to the users via the user interface $260_1$, $260_2$, . . . , $260_N$ to input data by the user to select at least one colour coding parameter.

In one embodiment of the present invention, the one or more colour coding parameters are selected from multiple different viscosity range of the colour composition to achieve the desired colour consistency composition in response to the input received by the user. Particularly, every colour code has a different colour viscosity data.

The method 800 proceeds to step 815. At step 815, the data associated with the colour code is registered and stored in the colour database 187 of the cloud server 180. Particularly, the data is based on the different colour viscosity associated with every colour code. Every colour code has a different colour viscosity and the data associated with the colour code is registered and stored in the colour database 187 of the cloud server 180. The method 800 proceeds to step 820. At step 820, the input data is processed to execute processor-executable code by the processor 182 enabling the cloud server 180 to perform actions, including, for each module of multiple modules on the colour mixing dispensing apparatus 105. In operation, each module of the multiple modules is capable of being used interoperably with other modules and multiple sub-modules without altering the other modules and sub-modules.

In one embodiment, multiple modules of the cloud server 180 includes the colour coding module 185 and the colour recipe parameter module 190. In operation, the colour coding module 185 is configured to process the data received from the user and store the data in the colour database 187. The data is the colour code recipe data to form many colour combinations. Subsequently, the colour recipe parameter module 190 is configured to execute and analyse the data received from colour coding module 185.

The method 800 proceeds to step 825. At step 825, the set of instructions for instant colour mixing is communicated to the colour mixing dispensing apparatus 105 at the defined time frame via the communication network 175. The method 800 proceeds to step 830. At step 830, a determination is made as to whether to activate operation of the controller member 108 to drive one or more drive gears 125 of the colour mixing dispensing apparatus 105 by validating the colour code recipe data provided by the user.

In one embodiment, if the determination is "YES" and the colour code recipe data is validated by retrieving the data from the colour database 187, the method 800 proceeds to step 835. At step 835, the colour code recipe data is analysed and set of instructions are executed by the controller module 158. Particularly, the collector member 192 of the colour mixing dispensing apparatus 105 receive the one or more desired colour consistency composition from one or more dispensers 150 from the cartridge 135. In operation, the colour code recipe data is analysed and based on the parameter of the viscosity sensed by the sensor 130. The sensor 130 is positioned over the elongated member 127 to provide sensing of the one or more parameters.

In another embodiment, if the determination is "NO" and the colour code recipe data is not validated by retrieving the data from the colour database 187, the method 800 proceeds to step 820. The method 800 proceeds to step 835. At step 835, the method 800 ends.

Figure 9:
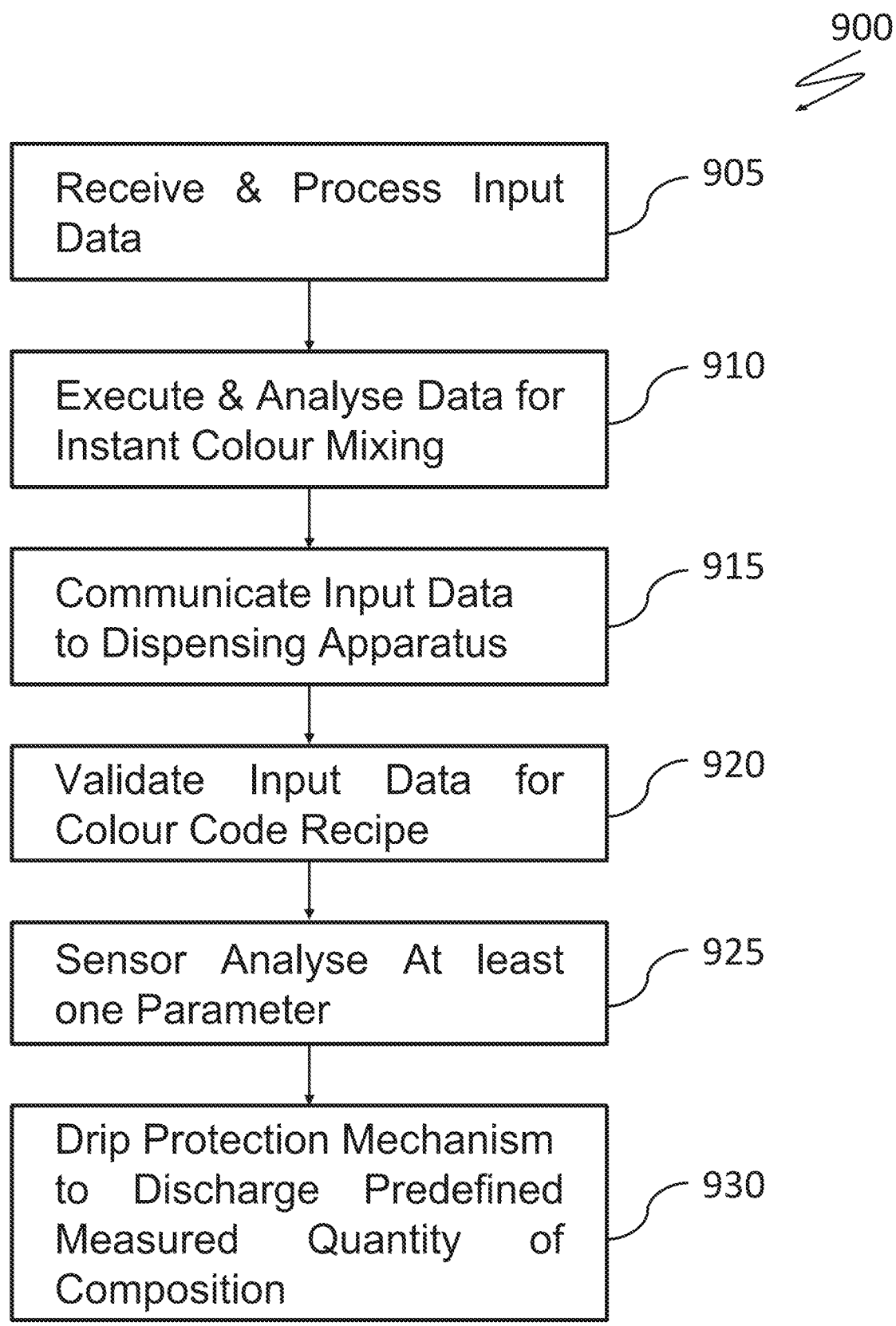
FIG. 9 is a flow diagram illustrating a method to process the input data received by the user and communicating the data to the colour mixing dispensing apparatus, according to one or more embodiments of the present invention.

FIG. 9 is a flow diagram illustrating a method 900 to process the input data received by the user and communicated to the colour mixing dispensing apparatus 105, according to one or more embodiments of the present invention. At step 905, the cloud server 180 receives the input data provided by the user for processing. The input data is communicated to the cloud server 180 for further analysis via the communication network 175. The user operates the user device 200 accessible via the user interface 260 to input data. The method 900 proceeds from step 905 to step 910. At step 910, the cloud server 180 is adapted to store data received from the user via the communication network 175. Particularly, the data obtained is the data for one or more colour coding parameters. In operation, the colour coding module 185 is configured to process the data received from the user and store the data in the colour database 187. Further, the colour recipe parameter module 190 is configured to execute and analyse the data received from colour coding module 185.

The method 900 proceeds from step 910 to step 915. At step 915, once the data received from colour coding module 185 is analysed the set of instructions for instant colour mixing is provided to the colour mixing dispensing apparatus 105 via the communication network 175 to be operated the defined time frame.

In one embodiment, the defined time frame is real time dispersion of the selected colours.

In another embodiment, the defined time frame is predefined time period for the operation of the colour mixing dispensing apparatus 105.

The method 900 proceeds from step 915 to step 920. At step 920, the colour code recipe data is validated by determining the colour code recipe data to activate operation of the controller member 108 to drive one or more drive gears 125. The method 900 proceeds from step 920 to step 925. At step 925, the one or more parameters are sensed by the one or more sensors 130.

Particularly, the one or more parameters are selected from anyone of minimum volume dispersion of one or more desired colour consistency composition dispensed from one or more cartridge members 135 and multiple different viscosity range of the colour composition. Further, the cartridge holder means 140 holds the cartridge member 135 in position to dispense the desired colour consistency composition once the one or more parameters are sensed by the one or more sensors 130.

The method 900 proceeds from step 925 to step 930, At step 930, the cartridge member 135 of each dispenser 150 is configured with a drip protection mechanism of discharging the desired colour consistency composition based on the set of instructions retrieved from the colour recipe parameter module 190.

The present technology is a boom in the industry 4.0 era. The colour coding recipe of the colour to be obtained is stored in the cloud server. Therefore, the present invention is able to provide colour consistency uniformly and same appeals to the end user. For example, the colour consistency in the nail polish or other cosmetic products which is a very important parameter for the end user. The overall cost is reduced in the long term as the wastage of the nail polish colour is reduced and there is no drying up of the nail paint. The texture and quality of the nail polish is preserved since the quantity of colour composition obtained is applicable for one application only, and there is no reuse.

At the same point of time the very important factor of hygiene is maintained in the overall execution of the present method deploying different components of the present system. In a scenario where the system is deployed in saloon the product obtained will only come in contact with one customer and the very important parameter of hygiene is solved.

Moreover, less storage space is required for storing the different colours and at the same point of time multiple colour combinations are obtained by automatic mixing of different colours to solve different problems of the prior arts. There is no limitation on the colour range which is produced by the implementation of the present system. Subsequently, the present invention is providing the capability of instant colour mixing to perform one or more activities. Overall the current cost of manufacturing processes is reduced due to one-time implementation of the technology. Real estate is getting costlier and so the one-time implementation saves the space for storing multiple colours in different containers.

What is claimed is:

1. A colour mixing dispensing apparatus to facilitate mixing of at least one colour to achieve a desired colour consistency to perform one or more activities comprising:
   a dispensing housing unit comprising a plurality of dispensers and each dispenser is housing a colour composition in a cartridge member configured to dispense measured quantity of said desired colour consistency composition to perform said one or more activities;
   a controller module comprising a dosing sub-module configured to control dispense of said desired colour consistency based on input data received from an user via a communication network, an activation sub-module configured to receive said set of instructions to activate operation of a controller member to drive at least one drive gear by validating and making a determination of colour code recipe data provided by said user, an execution sub-module configured to execute at least one colour coding parameter sensed by said at least one sensor and an analysis sub-module configured to analyse said at least one colour coding parameter; and
   a collector member to receive at least one desired colour consistency composition from said at least one dispenser from said cartridge member to generate instant colour mixing colour composition at a defined time frame to perform said one or more activities;
   wherein said colour mixing dispensing apparatus is configured to provide instant colour mixing to said user by receiving a set of instructions from a cloud server via said communication network and said cloud server comprises at least one memory adapted to store input data for said at least one colour coding parameter in a colour database and at least one processor that is adapted to execute processor-executable code;
   wherein, said at least one processor in response to execution, enables said cloud server to perform actions, including, for each module of a plurality of modules on said colour mixing dispensing apparatus and each module of said plurality of modules are capable of being used interoperably with other modules and a plurality of sub-modules without altering the other modules and sub-modules;
   wherein, said cartridge member is further configured to discharge said desired colour consistency composition based on said at least one colour coding parameter selected from anyone of minimum volume dispersion of one or more desired colour consistency composition dispensed from said at least one cartridge met ber and said at least one colour coding parameter is retrieved from said colour recipe parameter module from said cloud server;
   wherein said at least one colour coding parameter is selected from a plurality of different viscosity range to achieve said desired colour consistency composition in response to said input data received by said user and, said cartridge member is configured to discharge said at least one colour coding parameter selected from said plurality of different viscosity range dispensed from said at least one cartridge member and said at least one colour coding parameter is retrieved from said colour recipe parameter module from said cloud server; and
   wherein, said input data is a colour code recipe data and said input data is stored in said colour database.

2. The colour mixing dispensing apparatus as claimed in claim 1, wherein said colour mixing dispensing apparatus further comprises:
   an elongated member configured to mate with said at least one drive gear via said controller member and said at least one sensor positioned over said elongated member to sense said at least one colour coding parameter; and
   a cartridge holder means to hold said cartridge member in position to dispense said desired colour consistency composition;
   wherein; said controller member is a DC motor.

3. The colour mixing dispensing apparatus as claimed in claim 2, wherein said cloud server comprises a colour coding module configured to process said input data received from said user and store said data in said colour database and a colour recipe parameter module configured to execute and analyse said input data received from said colour coding module and providing a set of instructions for instant colour mixing to said colour mixing dispensing apparatus at a defined time frame.

4. The colour mixing dispensing apparatus as claimed in claim 1, wherein air pressure control is provided for operating said dispensing housing unit by said controller member of said dispenser.

5. The colour mixing dispensing apparatus as claimed in claim 3, wherein said defined time frame is any one selected from a pre-defined time period and real time dispersion of at least one selected colour provided by said input data.

6. The colour mixing dispensing apparatus as claimed in claim 1, wherein said one or more activities is any one selected from nail paint, gel for nail polish, face foundation and beauty cosmetic.

7. The colour mixing dispensing apparatus as claimed in claim 1, wherein said controller module is in electronic communication with a dispenser user interface and electrically powered by a power controller.

8. A method to facilitate mixing of at least one colour to achieve a desired colour consistency to perform one or more activities, said method comprising the steps of:

receiving input data by at least one user to select at least one colour coding parameter;

storing input data for said at least one colour coding parameter;

processing said input data to execute processor-executable code;

receiving a set of instructions to activate operation of controller member to drive at least one drive gear by validating and making a determination of said input data provided by said user;

providing motorized control for operating said dispensing housing unit by said controller member of said dispenser;

mating at least one drive gear with said controller member and an elongated member with said at least one drive gear; and sensing at least one parameter by at least one sensor position ed over said elongated member;

analysing said at least one colour coding parameter and executing said at least one colour coding parameter sensed by said at least one sensor;

communicating said input data to a controller module of a colour mixing dispensing apparatus via a communication network;

determining dispense of a desired colour consistency based on said input data by a dosing sub-module of said controller module to control dispense of said desired colour consistency based on said input data received from said user via said communication network;

generating instant colour mixing colour composition by said colour mixing dispensing apparatus at a defined time frame to perform said one or more activities wherein, said colour mixing dispensing apparatus comprises a dispensing housing unit and said dispensing housing unit comprises a plurality of dispensers;

wherein, at least one desired colour consistency composition from at least one dispenser is received and, each dispenser is housing a colour composition in a cartridge member, and each said cartridge member is dispensing measured quantity of colour into a collector member of said colour mixing dispensing apparatus based on said input data received via said communication network;

wherein said one or more activities is any one selected from nail paint, gel for nail polish; and wherein said input data is a colour code recipe data.

9. The method as claimed in claim 8, wherein said method further comprises the steps of:

activating operation of said controller member to drive said at least one drive gear by an activation sub module of said controller module;

determining validation of said input data by said activation sub module;

analysing said at least one colour coding parameter by an analysis sub-module of said controller module;

executing said at least one colour coding parameter by an execution sub-module of said controller module;

wherein said input data is stored in a colour database; and wherein said controller member is a DC motor.

* * * * *